United States Patent
Fang et al.

(10) Patent No.: US 11,579,117 B2
(45) Date of Patent: Feb. 14, 2023

(54) TEST DEVICE AND METHOD FOR TESTING AN OXIDATION POTENTIAL OF AN ELECTROLYT

(71) Applicants: Tsinghua University, Beijing (CN); HON HAI PRECISION INDUSTRY CO., LTD., New Taipei (TW)

(72) Inventors: Zhen-Han Fang, Beijing (CN); Jia-Ping Wang, Beijing (CN); Shou-Shan Fan, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 0 days.

(21) Appl. No.: 17/335,381

(22) Filed: Jun. 1, 2021

(65) Prior Publication Data
US 2022/0236217 A1 Jul. 28, 2022

(30) Foreign Application Priority Data
Jan. 26, 2021 (CN) .......................... 202110103980.8

(51) Int. Cl.
| | |
|---|---|
| G01J 3/00 | (2006.01) |
| G01N 27/416 | (2006.01) |
| G01N 33/44 | (2006.01) |
| G01N 21/66 | (2006.01) |

(52) U.S. Cl.
CPC ......... *G01N 27/4168* (2013.01); *G01N 21/66* (2013.01); *G01N 33/442* (2013.01)

(58) Field of Classification Search
CPC .. G01N 27/4168; G01N 21/66; G01N 33/442; Y02E 60/10
USPC .......................................................... 356/51
See application file for complete search history.

(56) References Cited

U.S. PATENT DOCUMENTS

| | | | | |
|---|---|---|---|---|
| 4,927,265 A | * | 5/1990 | Brownlee | G01N 21/64 |
| | | | | 204/603 |
| 2011/0164303 A1 | * | 7/2011 | Hampp | G02F 1/153 |
| | | | | 359/275 |

FOREIGN PATENT DOCUMENTS

CN 107154513 9/2017

OTHER PUBLICATIONS

Ta-Ming Liu et al., High ion-conducting solid polymer electrolytes based on blending hybrids derived from monoamine and diamine polyethers for lithium solid-state batteries, RSC Adv., 2017, 7, pp. 20373-20383.

* cited by examiner

*Primary Examiner* — Md M Rahman
(74) *Attorney, Agent, or Firm* — ScienBiziP, P.C.

(57) ABSTRACT

A test device for testing an oxidation potential of an electrolyte is provided. The test device comprises a cavity, a test unit, a detector, a processing unit, and a display. The test unit comprises a positive plate comprising a first through hole, a negative plate comprising a second through hole, a first infrared window covering the first through hole, a second infrared window covering the second through hole, and an electrolyte located between the positive electrode plate and the negative electrode plate. The first through hole and the second through hole penetrate each other. The first infrared window, the positive plate, the negative plate, and the second infrared window are stacked with each other. An infrared light beam passes through the first infrared window, the first through hole, the electrolyte, the second through hole, and the second infrared window in sequence and then is detected by the detector.

18 Claims, 19 Drawing Sheets

TEST DEVICE AND METHOD FOR TESTING AN OXIDATION POTENTIAL OF AN ELECTROLYT

CROSS-REFERENCE TO RELATED APPLICATIONS

This application claims all benefits accruing under 35 U.S.C. § 119 from China Patent Application No. 202110103980.8, filed on Jan. 26, 2021, in the China Intellectual Property Office, the contents of which are hereby incorporated by reference. The application is also related to copending applications entitled, "METHOD OF TESTING AN OXIDATION POTENTIAL OF ELECTROLYTE", filed Ser. No. 17/335,376; "GLYCERYL ETHER EPOXY RESIN AND METHOD FOR MAKING THE SAME", filed Ser. No. 17/335,387; "LITHIUM ION BATTERY ELECTROLYTE AND METHOD FOR MAKING THE SAME", filed 17/335,397.

FIELD

The present disclosure relates to a test device and a method for testing an oxidation potential of an electrolyte, in particular to a test device and a method for testing an oxidation potential of a lithium ion battery electrolyte.

BACKGROUND

With a gradual advancement of information terminal from a mainframe to wearable devices, demands for flexible electronic devices increases. As a key to flexible electronic devices, flexible energy storage devices are used as energy supply components in wearable electronic devices, implantable medical and other devices with broad application prospects. Compared with other mature energy storage devices, lithium-ion batteries (LIBs) have higher operating voltage and greater energy density, and thus the LIBs are considered to be ideal candidates for flexible energy storage devices.

Electrolyte is an important part of the lithium ion battery. An oxidation potential of the electrolyte directly affects the output voltage and energy density of the lithium ion battery. Whether the electrolyte is oxidized can be obtained by observing a peak change of an infrared spectrum of the electrolyte under a working state. However, conventional test devices and methods can not test the infrared spectrum of the electrolyte under the working state in-situ and dynamically.

Therefore, there is a need to provide a test device and method that can test the infrared spectrum of the electrolyte under the working state in situ and dynamically.

BRIEF DESCRIPTION OF THE DRAWINGS

Implementations of the present technology will now be described, by way of example only, with reference to the attached figures, wherein.

DETAILED DESCRIPTION

Figure 1:
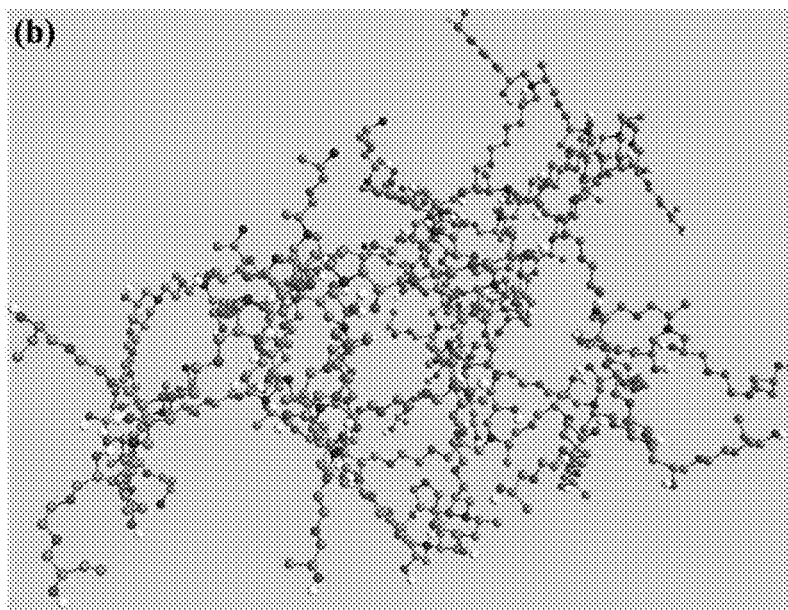
FIG. 1 is a schematic structural diagram of a cross-linked polyethylene glycol-based epoxy resin (c-PEGR) of one embodiment.

The disclosure is illustrated by way of example and not by way of limitation in the figures of the accompanying drawings in which like references indicate similar elements. It should be noted that references to "another," "an," or "one" embodiment in this disclosure are not necessarily to the same embodiment, and such references mean "at least one."

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale, and the proportions of certain parts have been exaggerated to better illustrate details and features of the present disclosure.

Several definitions that apply throughout this disclosure will now be presented.

The term "substantially" is defined to be essentially conforming to the particular dimension, shape, or other feature which is described, such that the component need not be exactly or strictly conforming to such a feature. The term "comprise," when utilized, means "include, but not necessarily limited to"; it specifically indicates open-ended inclusion or membership in the so-described combination, group, series, and the like.

A glyceryl ether epoxy resin according a first embodiment is provided. The glyceryl ether epoxy resin comprises an ether oxygen group. The glyceryl ether epoxy resin is a cross-linked polymer obtained by a ring-opening reaction of a glyceryl ether polymer and a polyamine compound. The glyceryl ether epoxy resin is a cross-linked three-dimensional network structure. The glyceryl ether polymer is a glycidyl ether polymer, and the glycidyl ether polymer comprises at least two epoxy groups. The polyamine compound comprises at least two amine groups. The cross-linked polymer comprises a main chain and a plurality of hydroxyl groups, and the plurality of hydroxyl groups are located on the main chain.

The plurality of hydroxyl groups is formed by the ring-opening reaction of the glycerol ether polymer and the polyamine compound. The plurality of hydroxyl groups is restricted to the main chain of the cross-linked polymer and unable to move freely. The ether oxygen group is (C—O—C)$_n$, and n is an integer greater than or equal to 1.

The glyceryl ether polymer is a glycidyl ether polymer, and the glycidyl ether polymer comprises at least two epoxy groups. The glyceryl ether polymer can be, but not limited to, poly(ethylene glycol) diglycidyl ether (PEGDE), poly(propylene glycol) diglycidyl ether, poly(ethylene oxide) diglycidyl ether, or combinations thereof. In one embodiment, the glyceryl ether polymer is the PEGDE, and a structural formula of the PEGDE is $C_3H_5O_2$—$(C_2H_4O)_n$—$C_3H_5O$, and n is an integer greater than or equal to 1. A monomer forming the glycidyl ether polymer can be allyl glycidyl ether, diglycidyl ether, isopropyl glycidyl ether, N-butyl glycidyl ether, aliphatic diglycidyl ether, phenyl glycidyl ether, or combinations thereof.

A molecular weight of the glyceryl ether polymer ranges from 200 to 600. If the molecular weight of the glyceryl ether polymer is too large, such as larger than 600, a viscosity of the cross-linked polymer is particularly large, and the main chain of the cross-linked polymer is particularly long and easy to entangle; on the contrary, if the molecular weight of the glycerol ether polymer is too small, such as smaller than 200, the main chain of the cross-linked polymer is too short, and a flexibility of the cross-linked polymer is poor. In one embodiment, the glyceryl ether polymer is the PEGDE, and a molecular weight of the PEGDE is 400.

The polyamine compound comprises at least two amine groups. The polyamine compound is formed by a polymerization reaction of organic amine. In one embodiment, the polyamine compound is an organic diamine polymer. The polyamine compound can be, but not limited to, polyether amine (PEA) polypropylene imine, polyethylene imine, polyepoxy amine, polyethylene diamine, polydiaminodiphenyl, polydiaminodiphenyl ether, or combinations thereof. In one embodiment, the polyamine compound is the PEA, and a structural formula of the PEA is $CH_3CH(NH_2)CH_2[OCH_2CH(CH_3)]_nNH_2$, and n is an integer greater than or equal to 1.

A molecular weight of the polyamine compound ranges from 1500 to 3000. If the molecular weight of the polyamine compound is too large, such as larger than 3000, a viscosity of the cross-linked polymer is particularly large, and the main chain of the cross-linked polymer is particularly long and easy to entangle; on the contrary, if the molecular weight of the polyamine compound is too small, such as smaller than 1500, the main chain of the cross-linked polymer is too short, and the flexibility of the cross-linked polymer is poor. In one embodiment, the molecular weight of the polyamine compound is 2000.

In one embodiment, the glyceryl ether polymer is the PEGDE; and the polyamine compound is the PEA. A chemical reaction formula of the ring-opening reaction of PEGDE and PEA is:

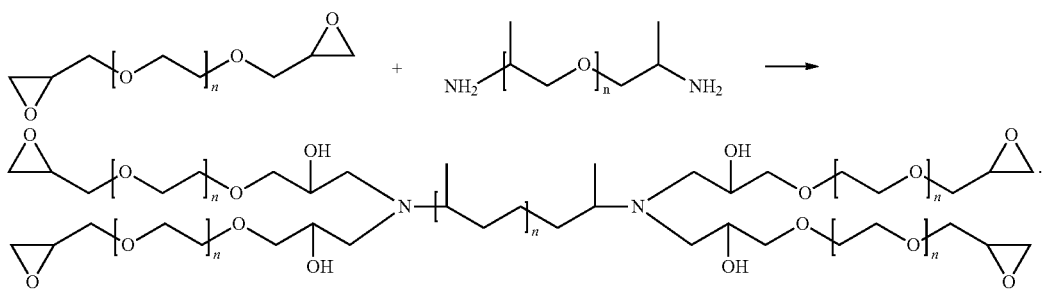

A cross-linked polyethylene glycol-based epoxy resin (c-PEGR) is formed by the ring-opening reaction of the PEGDE and the PEA. Referring to FIG. 1, the c-PEGR is a cross-linked three-dimensional network structure.

After the ring-opening reaction, a plurality of oxygen atoms in the epoxy groups of the PEGDE form the plurality of hydroxyl groups, and the plurality of hydroxyl groups are confined to the main chain of the c-PEGR by adjacent carbon atoms; and thus a freedom of movement of the plurality of hydroxyl groups is restricted, which greatly reduced a possibility of oxidation of the plurality of hydroxyl groups of the c-PEGR. Therefore, an oxidation stability of the c-PEGR is significantly improved. Experiments show that an oxidation potential of the c-PEGR can reach 4.36V. An ethylene oxide (EO) structure and a propylene oxide (PO) structure are remained on the main chain of the c-PEGR. When the c-PEGR is used in an electrolyte of a lithium ion battery, having excellent compatibility with the Li metal anode. The c-PEGR is polymerized by a PEG-based reactant modified with terminal epoxy groups and a PEG-based reactant modified with terminal amino groups; therefore, the c-PEGR has excellent flexibility.

A method of making the glyceryl ether epoxy resin is also provided. The method comprises steps of:

step (S1): providing the glyceryl ether polymer, the polyamine compound, and a substrate;

step (S2): mixing the glycerol ether polymer and the polyamine compound to form a precursor;

step (S3): coating the precursor on a surface of the substrate; and step (S4): heating the substrate coated with the precursor to obtain the glyceryl ether epoxy resin.

In step (S1), the glycerol ether polymer and the polyamine compound can be formulated in equal equivalents according to an epoxy equivalent and an amine equivalent.

In step (S2), the glyceryl ether polymer and the polyamine compound can be mixed according to a certain mass ratio. A mass ratio between the glycerol ether polymer and the polyamine compound can be ranged from 1:4 to 4:5. In one embodiment, the mass ratio between the glycerol ether polymer and the polyamine compound is ranged from 2:4 to 4:5. In one embodiment, the mass ratio between the glycerol ether polymer and the polyamine compound is 2:5.

In one embodiment, in step (S2), in order to make the glycerol ether polymer and polyamine compound well mixed, after mixing the glycerol ether polymer and the polyamine compound, further heating a mixture of the glycerol ether polymer and the polyamine compound to a temperature, and keeping stirring the mixture at the temperature for a period of time to obtain the precursor. Stirring the mixture can be implemented by electric stirring or magnetic stirring. In one embodiment, after mixing the glycerol ether polymer and the polyamine compound, further heating the mixture of the glycerol ether polymer and the polyamine compound to a temperature ranged from 50° C. to 60° C., and keeping stirring the mixture at the temperature ranged from 50° C. to 60° C. for 12-48 hours. In one embodiment, after mixing the glycerol ether polymer and the polyamine compound, further heating the mixture of the glycerol ether polymer and the polyamine compound to 55° C., and keeping stirring the mixture at 55° C. for 20 hours.

In step (S3), in one embodiment, the substrate has a flat surface. A shape and a size of the substrate can be selected according to actual needs. A material of the substrate can be polyolefin. In one embodiment, the material of the substrate is poly tetra fluoroethylene (PTFE).

In step (S4), in one embodiment, heating the substrate coated with the precursor to a temperature ranged from 80° C. to 90° C., and keeping the substrate coated with the precursor at the temperature ranged from 80-90° C. for 30-55 hours. In one embodiment, heating the substrate coated with the precursor to 85° C., and keeping the substrate coated with the precursor at 85° C. for 30-55 hours.

In one embodiment, the cross-linked polyethylene glycol-based epoxy resin (c-PEGR) is obtained by the method of making the glyceryl ether epoxy resin. A method of making the c-PEGR comprises: formulating the PEGDE and the PEA in equal equivalents according to the epoxy equivalent and the amine equivalent; mixing the PEGDE and the PEA according to a mass ratio PEGDE:PEA=2:5, and magnetically stirring a mixture of the PEGDE and the PEA at 55° C. for 20 hours to form the precursor; coating the precursor uniformly on a surface of a PTFE substrate; and heating the PTFE substrate coted with the precursor to 85° C., and keeping the PTFE substrate coated with the precursor at 85° C. for 48 hours, to obtain the c-PEGR.

Figure 2:
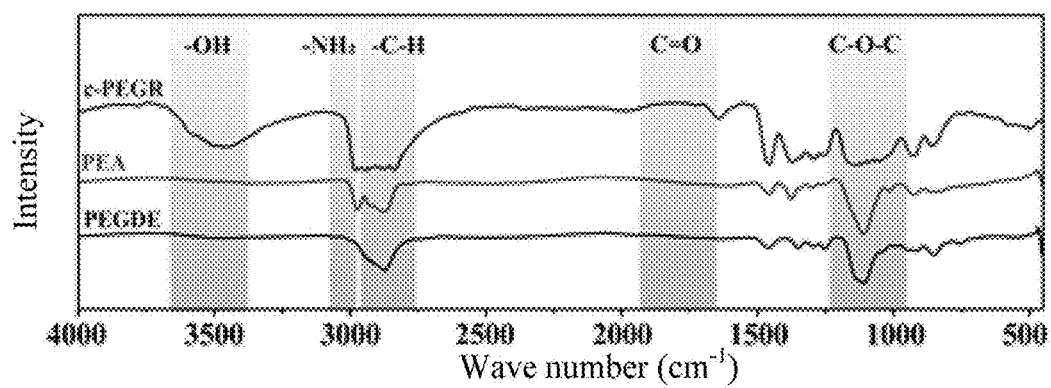
FIG. 2 is a Fourier transform infrared spectroscopy (FTIR) of a reaction process of a method for making the c-PEGR in FIG. 1.

FIG. 2 is a Fourier transform infrared spectroscopy (FTIR) of a reaction process for the method of making the c-PEGR in one embodiment. It can be seen that two major peaks are detected near 1100 cm$^{-1}$ and 2800 cm$^{-1}$ in the reactants PEGDE and PEA, respectively, corresponding to the stretching vibrations of the ether group (C—O—C) and the carbon-hydrogen bond in the main chain repeating unit, respectively. Furthermore, the PEA exhibits an additional stretching vibration peak near 3000 cm$^{-1}$ in the FTIR spectrum due to a presence of the amino group. The c-PEGR exhibits a stretching vibration peak of the hydroxyl group near 3500 cm$^{-1}$, indicating the c-PEGR produced by the ring-opening reaction of the PEGDE and the PEA comprises the hydroxyl group, which is consistent with the reaction formula of the PEGDE and the PEA.

Figure 3:
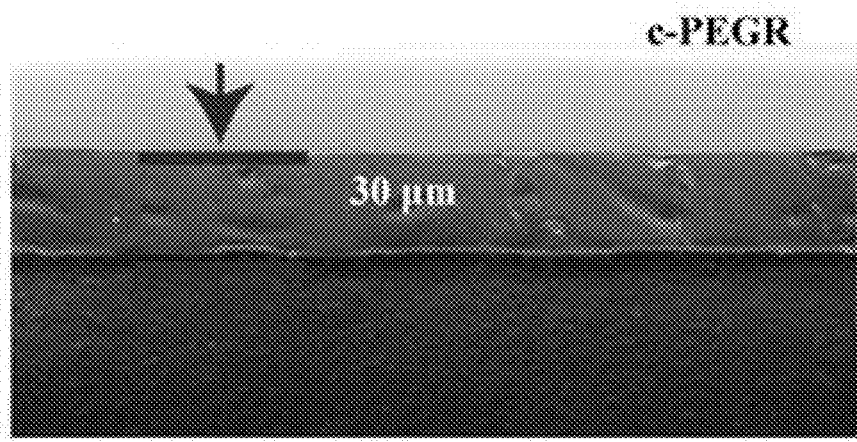
FIG. 3 is a scanning electron micrograph of one embodiment of the c-PEGR.

FIG. 3 shows a scanning electron micrograph (SEM) of the c-PEGR obtained in one embodiment. It can be seen from FIG. 3 that a thickness of the c-PEGR is about 30 μm.

The glyceryl ether epoxy resin is polymerized by a polyglyceryl ether-based reactant modified with terminal group (epoxy group) and a polyglyceryl ether-based reactant modified with terminal group (amino group), and the glyceryl ether epoxy resin contains the ether oxygen groups. Therefore, the glyceryl ether epoxy resin has excellent flexibility. The glyceryl ether epoxy resin has a cross-linked three-dimensional network structure, and thus the glyceryl ether epoxy resin has excellent mechanical properties and a strong structure. The hydroxyl groups of the glyceryl ether epoxy resin are confined to the main chain of the glyceryl ether epoxy resin; and thus the freedom of movement of the hydroxyl groups is restricted, which greatly reduced the possibility of oxidation of the hydroxyl groups of the glyceryl ether epoxy resin. Therefore, the oxidation stability of the glyceryl ether epoxy resin is significantly improved, and the oxidation potential of the glyceryl ether epoxy resin can reach 4.36V. Furthermore, the ethylene oxide (EO) structure and the propylene oxide (PO) structure are remained on the main chain of the glyceryl ether epoxy resin. When the glyceryl ether epoxy resin is used in an electrolyte of lithium ion batteries, having excellent compatibility with the Li metal anode.

Figure 4:
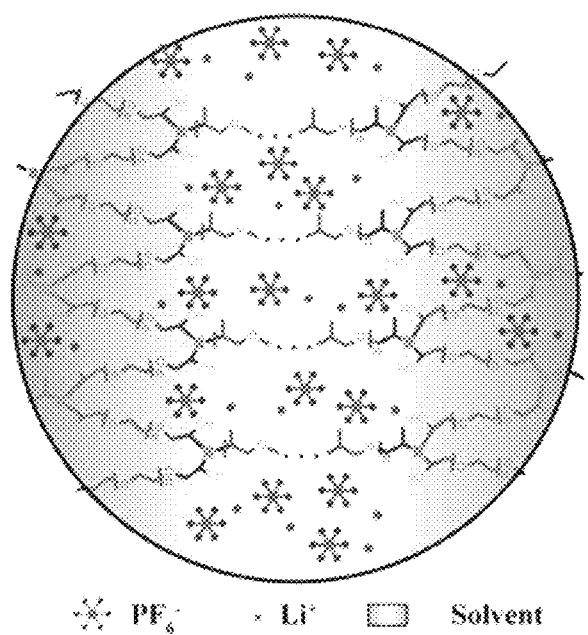
FIG. 4 is a schematic structure diagram of a lithium ion battery electrolyte of one embodiment.

Referring to FIG. 4, a lithium ion battery electrolyte 100 according one embodiment is provided. The lithium ion battery electrolyte 100 comprises a glyceryl ether epoxy resin gel 10. The glyceryl ether epoxy resin gel 10 comprises a glyceryl ether epoxy resin 12 and an electrolyte 14. The glyceryl ether epoxy resin 12 is a cross-linked three-dimensional network structure. The electrolyte 14 comprises a lithium salt 142 and a non-aqueous solvent 144. The lithium salt 142 is interspersed in the cross-linked three-dimensional network structure of the glyceryl ether epoxy resin 12. The lithium salt 142 and the glyceryl ether epoxy resin 12 are dispersed in the non-aqueous solvent 142. In one embodiment, the lithium ion battery electrolyte 100 consists of the glyceryl ether epoxy resin gel 10; the glyceryl ether epoxy resin gel 10 consists of the glyceryl ether epoxy resin 12 and the electrolyte 14.

The glyceryl ether epoxy resin 12 is the same as the glyceryl ether epoxy resin in the first embodiment, and comprises all features of the glyceryl ether epoxy resin in the first embodiment. In order to save space, the features of the glyceryl ether epoxy resin 12 are not repeated.

The electrolyte 14 can be an existing lithium ion battery electrolyte. In one embodiment, the electrolyte 14 is (1M LiPF$_6$ in DMC:FEC=1:1 vol %), that is, the electrolyte 14 is formed by adding 1 mol/L lithium hexafluorophosphate (LiPF$_6$) to a non-aqueous solvent of dimethyl carbonate (DMC) and fluoroethylene carbonate (FEC) with a volume ratio of 1:1.

The lithium salt 142 can be lithium chloride (LiCl), Lithium hexafluorophosphate (LiPF$_6$), Lithium tetrafluoroborate (LiBF$_4$), lithium methanesulfonate (LiCH$_3$SO$_3$), lithium trifluoromethanesulfonate (LiCF$_3$SO$_3$), lithium hexafluoroarsenate (LiAsF$_6$), lithium hexafluoroantimonate (LiSbF$_6$), lithium perchlorate (LiClO$_4$), Li[BF$_2$(C$_2$O$_4$)], Li[PF$_2$(C$_2$O$_4$)$_2$], Li[N(CF$_3$SO$_2$)$_2$], Li[C(CF$_3$SO$_2$)$_3$], lithium bisoxalate borate (LiBOB), or combinations thereof.

The non-aqueous solvent 144 can be selected from cyclic carbonates, linear carbonates, cyclic ethers, linear ethers, nitriles, and amides, and can be at least one of ethylene carbonate (EC), propylene carbonate (PC), ethylmethyl carbonate (EMC), diethyl carbonate (DEC), dimethyl carbonate (DMC), butylenes carbonate, vinylene carbonate, methylethyl carbonate, methyl acetate, ethyl acetate, propyl acetate, methyl propionate, ethyl propionate, y-butyrolactone, 1,2dimethoxyethane, 1,2-diethoxyethane, tetrahydrofuran, 1,2-dioxane, 2-methyltetrahydrofuran, acetonitrile, and dimethylformamide.

In one embodiment, the glyceryl ether epoxy resin gel 10 is the cross-linked polyethylene glycol-based epoxy resin (c-PEGR) gel, the glyceryl ether epoxy resin 12 is the c-PEGR as the first embodiment, the lithium salt 142 is the lithium hexafluorophosphate (LiPF$_6$), and the non-aqueous solvent 144 is DMC and FEC.

A method of making the lithium ion battery electrolyte 100 is also provided. The method comprises steps of:

step (S'1): providing the glyceryl ether epoxy resin 12; and step (S'2): immersing the glyceryl ether epoxy resin 12 in the electrolyte 14 to obtain the glyceryl ether epoxy resin gel 10.

In the step (S'1), a method of making the glyceryl ether epoxy resin 12 is the same as the method of making the glyceryl ether epoxy resin in the first embodiment.

Figure 5:
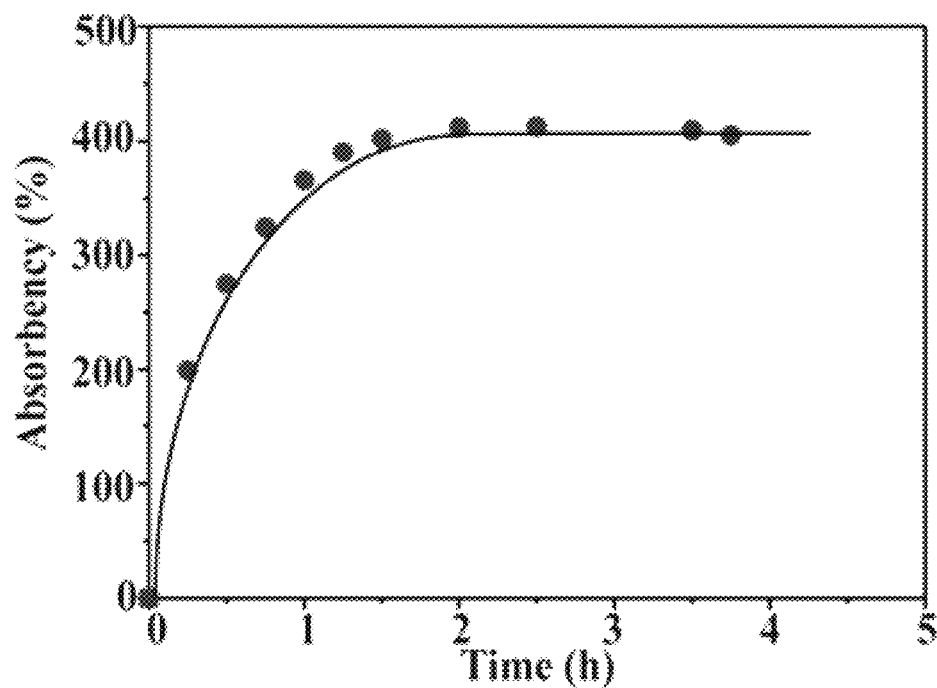
FIG. 5 is a curve of an absorbance of a c-PEGR gel with a time immersing in an electrolyte.

In the step (S'2), a time of immersing the glyceryl ether epoxy resin 12 in the electrolyte 14 is greater than or equal to 2 hours. FIG. 5 shows a curve of an absorbance of the c-PEGR gel with the time immersing in the electrolyte, the absorbance refers to a ratio of a current mass of the c-PEGR gel to an initial mass of the c-PEGR gel. It can be seen that after the c-PEGR gel immersing in the electrolyte for 2 hours, a mass of the c-PEGR gel reached saturation. At this time, the current mass of the c-PEGR gel is about 400% of the initial mass of the c-PEGR gel.

In one embodiment, the lithium ion battery electrolyte 100 is the c-PEGR gel electrolyte, the glyceryl ether epoxy resin gel 10 is the c-PEGR gel, and the electrolyte 14 is (1M LiPF$_6$ in DMC:FEC=1:1 vol %), the lithium salt 142 is lithium hexafluorophosphate (LiPF$_6$), and the non-aqueous solvent 144 is DMC and FEC. The c-PEGR gel electrolyte is obtained by the method of making the lithium ion battery electrolyte 100. A method of making the c-PEGR gel electrolyte comprises: formulating the PEGDE and the PEA in equal equivalents according to the epoxy equivalent and the amine equivalent; mixing the PEGDE and the PEA according to a mass ratio PEGDE:PEA=2:5, and magnetically stirring a mixture of the PEGDE and the PEA at 55° C. for 20 hours to form the precursor; coating the precursor uniformly on a surface of a PTFE substrate; and heating the PTFE substrate coated with the precursor to 85° C., and keeping the PTFE substrate coted with the precursor at 85° C. for 48 hours, to obtain the c-PEGR; providing the electrolyte (1M LiPF$_6$ in DMC:FEC=1:1 vol %), and immersing the c-PEGR in the electrolyte for 2 hours to obtain the c-PEGR gel.

Figure 6:
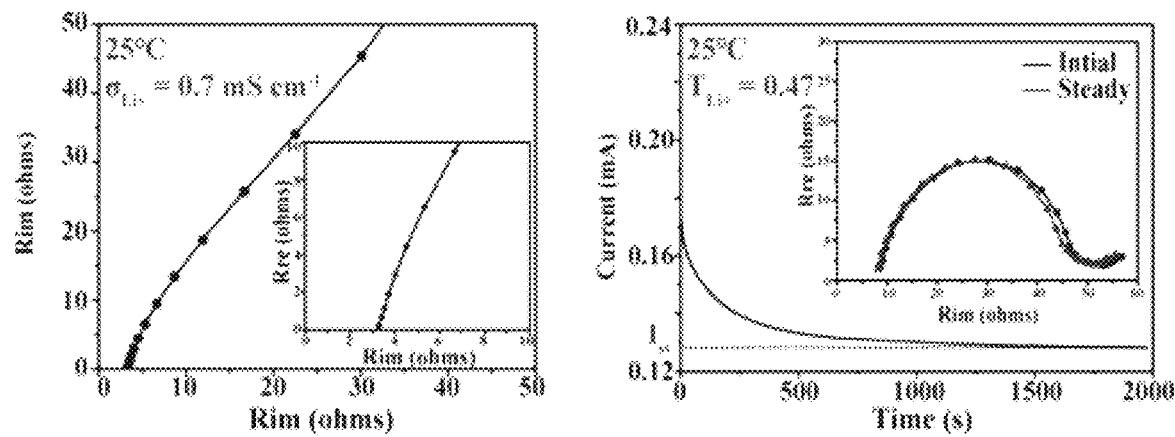
FIG. 6 is a change curve of an ionic conductivity of a c-PEGR gel electrolyte in a first button cell and a change curve of a Li-ion transfer number of the c-PEGR gel electrolyte in a second button cell.

The glyceryl ether epoxy resin gel 10 comprises the glyceryl ether epoxy resin and the electrolyte 14, the electrolyte 14 has superior Li ion conductivity, and the glyceryl ether epoxy resin mainly plays a role of storing electrolyte. Therefore, the glyceryl ether epoxy resin is not dominant in a transfer process of Li ions, which greatly improves an ionic conductivity and Li-ion transfer number of the glyceryl ether epoxy resin gel electrolyte. A first button cell is assembled by using a stainless steel electrode coated with gold as working electrode, reference electrode and counter electrode; and using the c-PEGR gel electrolyte as the electrolyte, to test the ionic conductivity of the c-PEGR gel electrolyte. A second button cell is assembled by using a lithium electrode as working electrode, reference electrode and counter electrode; and using the c-PEGR gel electrolyte as the electrolyte, to test the Li-ion transfer number c-PEGR gel electrolyte. FIG. 6 shows a change curve of the ionic conductivity of the c-PEGR gel electrolyte in the first button cell and a change curve of the Li-ion transfer number of the c-PEGR gel electrolyte in the second button cell. It can be seen that the ionic conductivity of the c-PEGR gel electrolyte at room temperature (25° C.) is 0.7 mS cm$^{-1}$, and the Li-ion transfer number of the c-PEGR gel electrolyte at room temperature is 0.47, the ionic conductivity and the Li-ion transfer number of the c-PEGR gel electrolyte are both comparable to that of a liquid electrolyte (LE).

Figure 7:
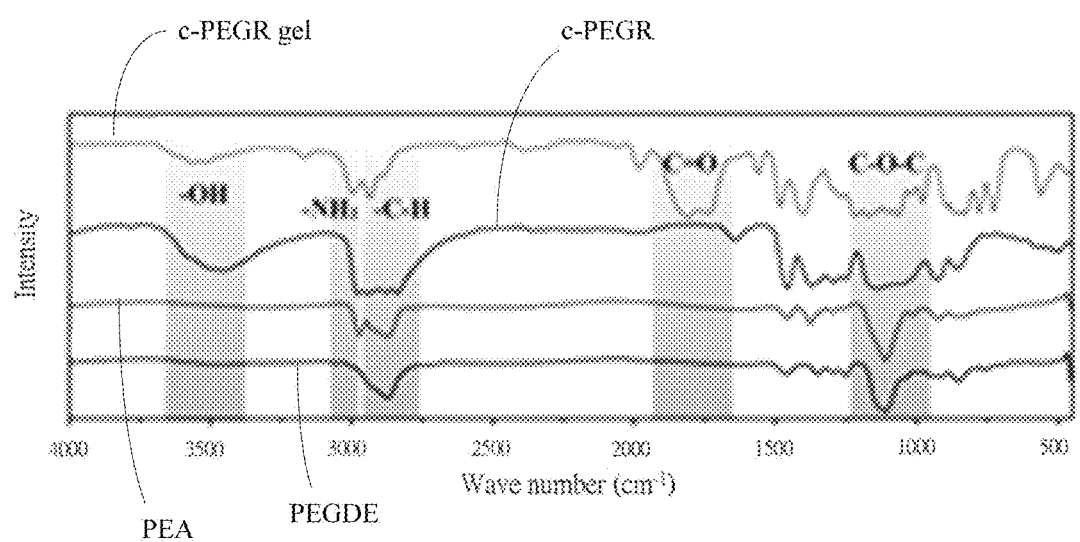
FIG. 7 shows a Fourier transform infrared spectroscopy (FTIR) of one embodiment of a c-PEGR.

FIG. 7 shows a Fourier transform infrared spectroscopy (FTIR) of the c-PEGR gel in one embodiment. It can be seen that, the c-PEGR gel shows a stretching vibration peak of the hydroxyl group near 3500 cm$^{-1}$; compared to the c-PEGR, a stretching vibration peak at 1800 cm$^{-1}$ is shown in the curve of c-PEGR gel due to a presence of a carbonyl group (C=O) in the non-aqueous solvent 144.

In order to test extraction and insertion of lithium in a lithium anode of lithium ion battery electrolyte 100, the LE is sandwiched between two non-blocking Li electrodes and assembled into a Li∥LE∥Li symmetric cell; the c-PEGR gel electrolyte is sandwiched between two non-blocking Li electrodes and assembled into a Li∥c-PEGR gel∥Li symmetric cell; and a cross-linked polyethylene glycol (PEG) gel electrolyte is sandwiched between two non-blocking Li electrodes and assembled into a Li∥PEG gel∥Li symmetric cell. In the Li∥LE∥Li symmetric cell, Li∥c-PEGR gel∥Li symmetric cell and Li∥PEG gel∥Li symmetric cell, only the electrolyte is different, the other materials and structures are all the same.

Figure 8:
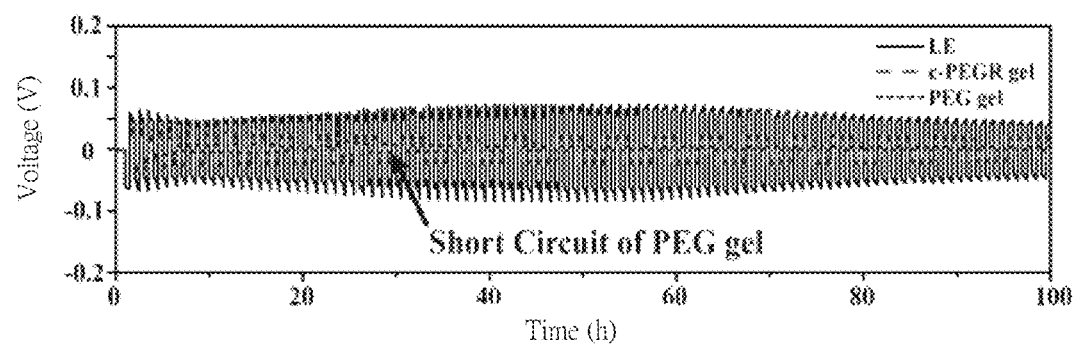
FIG. 8 shows voltage curves of Li∥Liquid electrolyte (LE)∥Li symmetric cell, Li∥c-PEGR gel∥Li symmetric cell and Li∥PEG gel∥Li symmetric cell when a current density is 0.2 mA cm$^{-2}$.

FIG. 8 shows the voltage curves of all the Li∥LE∥Li symmetric cell, Li∥c-PEGR gel∥Li symmetric cell and Li∥PEG gel∥Li symmetric cell when a current density is 0.2 mA cm$^{-2}$. It can be seen that from FIG. 8, compared to the Li∥LE∥Li symmetric cell and the Li∥PEG gel∥Li symmetric cell, the voltage curve of the Li∥c-PEGR gel∥Li symmetric cell is more stable, and has smaller polarization voltage.

Figure 9:
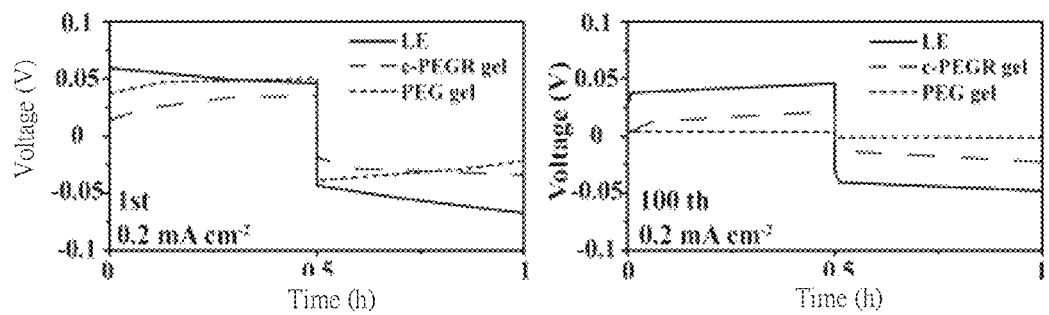
FIG. 9 shows voltage curves of the Li∥LE∥Li symmetric cell, Li∥c-PEGR gel∥Li symmetric cell and Li∥PEG gel∥Li symmetric cell during a 1st cycle and a 100th cycle.

FIG. 9 shows the voltage curves of all the Li∥LE∥Li symmetric cell, Li∥c-PEGR gel∥Li symmetric cell and Li∥PEG gel∥Li symmetric cell during the 1st cycle and the 100th cycles. It can be seen that from FIG. 9, a flat voltage platform of the Li∥c-PEGR gel∥Li symmetric cell in both the charged and discharged states can be maintained throughout the cycle, and the flat voltage platform is about 25 mV. It can also be seen that from FIG. 9, a voltage platform of the Li‖LE‖Li symmetric cell in both the charged and discharged states throughout the cycle is about 50 mV; and an initial overpotential of the Li‖PEG gel‖Li symmetric cell is close to 50 mV, due to the lack of structural stability of the Li‖PEG gel‖Li symmetric cell, the Li‖PEG gel‖Li symmetric cell is hardly inhibit a penetration of Li dendrites and the short circuit occurred, which is manifested by a sudden voltage drop during the cycling process of the Li‖PEG gel‖Li symmetric cell. Therefore, the c-PEGR gel electrolyte has a lower overpotential compared to the LE and the PEG gel electrolyte, indicating that the c-PEGR gel electrolyte making the Li-ion stripping/plating process much more accessible to Li metal surfaces.

Figure 10:
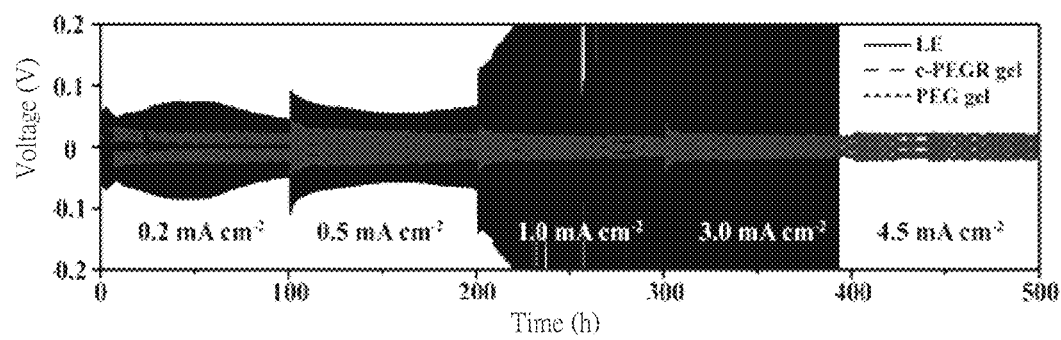
FIG. 10 shows at different current densities, voltage curves of the Li∥LE∥Li symmetric cell, Li∥c-PEGR gel∥Li symmetric cell and Li∥PEG gel∥Li symmetric cell during the 1st cycle and the 100th cycle.

FIG. 10 shows at different current densities, the voltage curves of the Li‖LE‖Li symmetric cell, Li‖c-PEGR gel‖Li symmetric cell and Li‖PEG gel‖Li symmetric cell during the 1st cycle and the 100th cycles. It can be seen that from FIG. 10, at different current densities, the Li‖c-PEGR gel‖Li symmetric cell shows excellent cycle stability and continuous low polarization voltage; however, when the current density is higher than 1 mA cm$^{-2}$, for both the Li‖LE‖Li symmetric cell and the Li‖PEG gel‖Li symmetric cell, an inhomogeneity of the Li metal stripping/plating process is severe, exacerbating a behavior of dendrite growth, dead Li generation, and a constant consumption of electrolyte by SEI on the Li metal surface.

FIGS. 8-10 illustrate that compared to the lithium symmetric batteries using the LE and the PEG gel electrolyte, the lithium symmetric battery using the c-PEGR gel electrolyte in present invention has more stable voltage and cycle performance.

Figure 11:
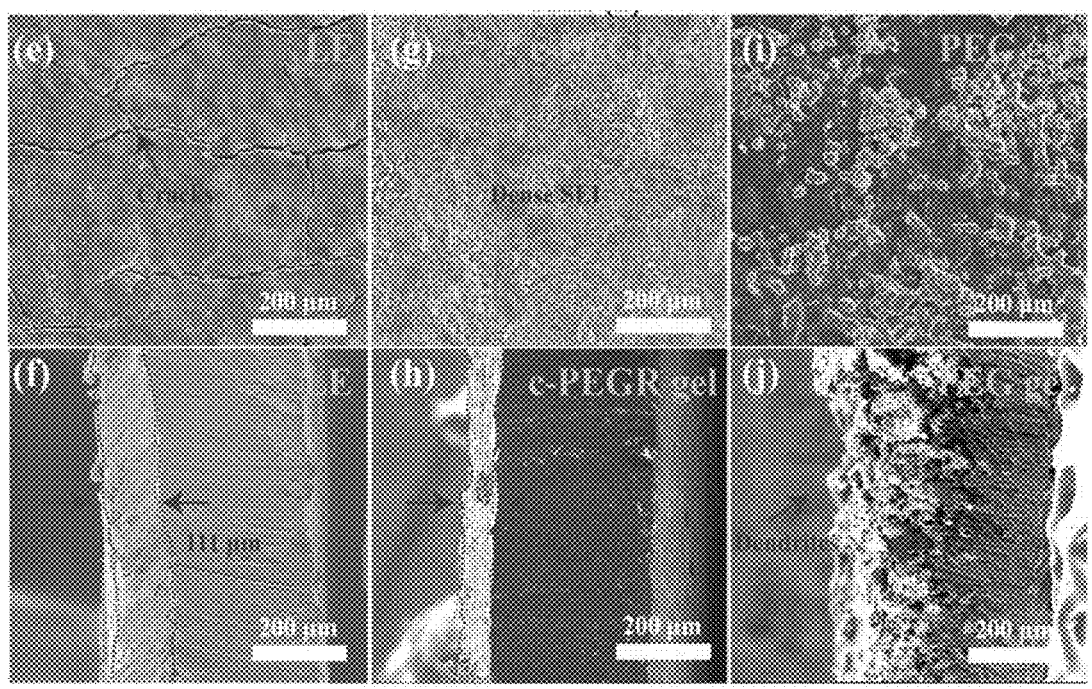
FIG. 11 shows a frontal morphology and a cross-sectional morphology of Li cycled in electrolytes of the Li∥LE∥Li symmetric cell, the Li∥c-PEGR gel∥Li symmetric cell and the Li∥PEG gel∥Li symmetric cell after cycled for 100 hours at a current density of 0.2 mA cm$^{-2}$.

FIG. 11 illustrates a frontal morphology and a cross-sectional morphology of Li cycled in the electrolyte of the Li‖LE‖Li symmetric cell, the Li‖c-PEGR gel‖Li symmetric cell and the Li‖PEG gel‖Li symmetric cell after cycled for 100 hours at a current density of 0.2 mA cm$^{-2}$. It can be seen that from FIG. 11, a layer of SEI with a thickness of 111 μm and distinct cracks are observed on a surface of the Li cycled in the LE. These cracks indicate that the SEI generated by the LE is unstable and that the LE may be able to come into contact with the newly exposed Li through these cracks, leading to further SEI thickening and electrolyte consumption. It can also be seen that a plurality of inhomogeneous distributions of dendritic particles can be observed on the surface and side of the Li cycled in the PEG gel electrolyte, which explains why it was prone to short-circuiting. However, the surface of the Li cycled in the c-PEGR gel electrolyte formed a thinner (58 μm) and more dense SEI, which effectively prevented Li dendrite growth and further electrolyte consumption. Therefore, compared with the Li‖LE‖Li symmetric cell and the Li‖c-PEGR gel‖Li symmetric cell, a cycle performance of the Li‖c-PEGR gel‖Li symmetric cell is greatly improved.

In a argon glove box, lithium cobalt oxide (LCO) is used as a working electrode, a lithium foil is used as counter electrode and reference electrode, and the LE, the c-PEGR gel electrolyte and the PEG gel electrolyte are used as electrolytes respectively, to assemble a LCO‖LE‖Li coin cell, a LCO‖PEG gel‖Li coin cell, and LCO‖c-PEGR gel‖Li coin cell respectively. In the LCO‖LE‖Li coin cell, the LCO‖PEG gel‖Li coin cell, and the LCO‖c-PEGR gel‖Li coin cell, only the electrolyte is different, the other materials and structures are all the same.

Figure 12:
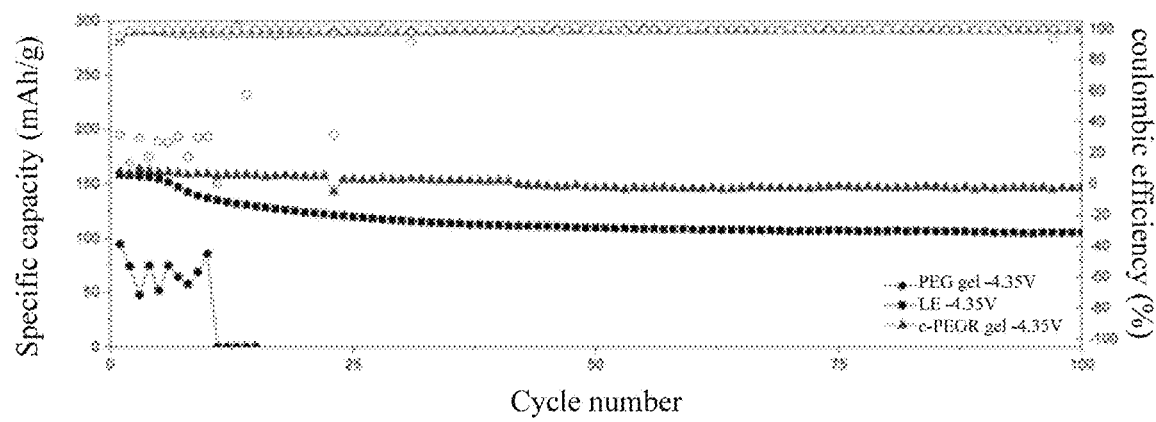
FIG. 12 shows cycle performance of the LCO∥LE∥Li coin cell, the LCO∥PEG gel∥Li coin cell, and the LCO∥c-PEGR gel∥Li coin cell at 0.2C rate.

FIG. 12 illustrates a cycle performance of the LCO‖LE‖Li coin cell, the LCO‖PEG gel‖Li coin cell, and the LCO‖c-PEGR gel‖Li coin cell at 0.2C rate. It can be seen from FIG. 12 that when a cutoff voltage is increased to 4.35 V, the LCO‖c-PEGR gel‖Li coin cell is still able to operate, exhibiting an initial capacity of 159.1 mAh g-1 and retaining 146.3 mAh g$^{-1}$ capacity after 100 cycles, with 91.95% capacity retention and 99.92% average coulombic efficiency. Both the capacity retention and the average coulombic efficiency of the LCO‖c-PEGR gel‖Li coin cell are higher than that of the LCO‖LE‖Li coin cell and the LCO‖PEG gel‖Li coin cell. Due to the LCO‖PEG gel‖Li coin cell has poor oxidation stability, the LCO‖PEG gel‖Li coin cell exhibits unstable capacity and low coulombic efficiency when working under high voltage, and after 10 cycles, the capacity cannot be released at all. Therefore, compared to the LCO‖LE‖Li coin cell and the LCO‖PEG gel‖Li coin cell, the LCO‖c-PEGR gel‖Li coin cell shows better cycle stability and coulombic efficiency.

Figure 13:
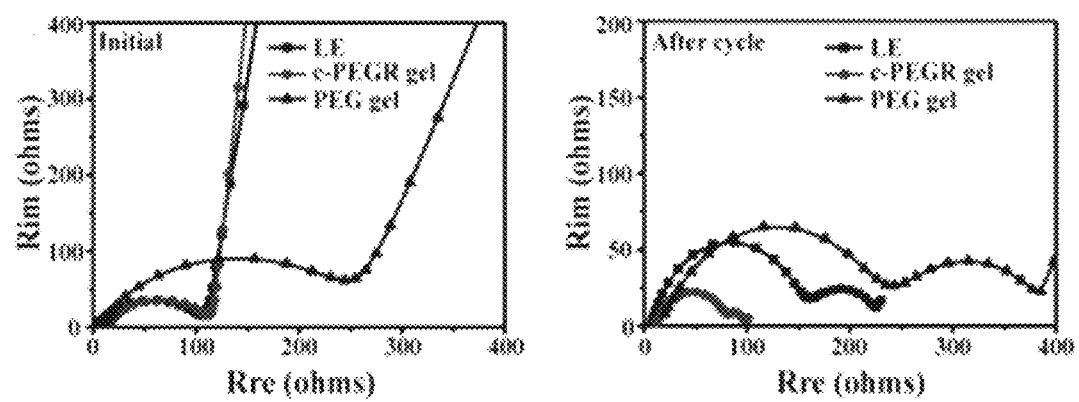
FIG. 13 shows electrochemical impedance spectroscopyin (EIS) of the LCO∥LE∥Li coin cell, the LCO∥PEG gel∥Li coin cell, and the LCO∥c-PEGR gel∥Li coin cell at an initial stage and after cycling.

FIG. 13 shows electrochemical impedance spectroscopyin (EIS) of the LCO‖LE‖Li coin cell, the LCO‖PEG gel‖Li coin cell, and the LCO‖c-PEGR gel‖Li coin cell at an initial stage and after cycling. It can be seen that from FIG. 13, a charge transfer resistance of the LCO‖c-PEGR gel‖Li coin cell is 101.9Ω, a charge transfer resistance of the LCO‖LE‖Li coin cell is 102.3Ω. Therefore, there is no significant difference between the charge transfer resistance of the LCO‖c-PEGR gel‖Li coin cell and the charge transfer resistance of the LCO‖LE‖Li coin cell, this is because the c-PEGR gel electrolyte comprises the LE, and the c-PEGR gel electrolyte has excellent flexibility, and thus the c-PEGR gel electrolyte can fully contact the electrode. However, the LCO‖PEG gel‖Li coin cell exhibits a higher charge transfer impedance of 265.7Ω in the initial state, due to a poor structural stability of the PEG gel. It can also be seen that from FIG. 13, after cycling at 0.2C, a charge transfer resistance at the cathode interface and a charge transfer resistance at the anode interface of the LCO‖c-PEGR gel‖Li coin cell are 71.2Ω and 25.5Ω, respectively; a charge transfer resistance at the cathode interface and a charge transfer resistance at the anode interface of the LCO‖LE gel‖Li coin cell are 156.5Ω and 81.5Ω, respectively; and a charge transfer resistance at the cathode interface and a charge transfer resistance at the anode interface of the LCO‖PEG gel‖Li coin cell are 239.9Ω and 183.4Ω. Therefore, the charge transfer resistance at the cathode interface and the charge transfer resistance at the anode interface of the LCO‖c-PEGR gel‖Li coin cell are much lower than those of the LCO‖LE gel‖Li coin cell and the LCO‖PEG gel‖Li coin cell, which indicates that the c-PEGR gel electrolyte shows the best lithium ion transfer ability, and a minimum thickness of a passivation layer generated and the easiest transfer of Li ions in the LCO‖c-PEGR gel‖Li coin cell.

Figure 14:
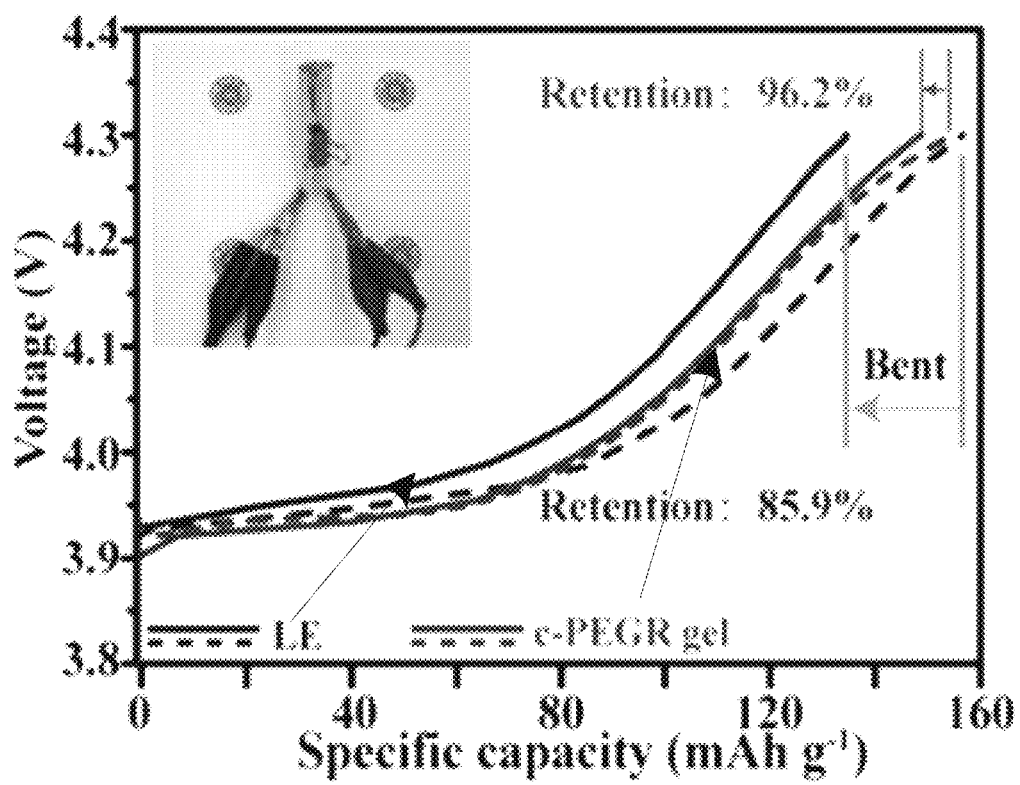
FIG. 14 shows voltage-capacity curves for a first charge of the LCO∥c-PEGR gel∥Li coin cell and the LCO∥LE gel∥Li coin cell at a rate of 0.1C, respectively.

FIG. 14 shows a voltage-capacity curve for a first charge of the LCO‖c-PEGR gel‖Li coin cell and the LCO‖LE gel‖Li coin cell at a rate of 0.1C, respectively. It can be seen that from FIG. 14, an initial charging capacity of the LCO‖c-PEGR gel‖Li coin cell and an initial charging capacity of the LCO‖LE gel‖Li coin cell are not much variation. The initial charging capacity of the LCO‖c-PEGR gel‖Li coin cell is 154.7 mAh g$^{-1}$, and the initial charging capacity of the LCO‖LE gel‖Li coin cell is 156.7 mAh g$^{-1}$. However, after the LCO‖c-PEGR gel‖Li coin cell and the LCO‖LE gel‖Li coin cells are bent (FIG. 14 inset), a significant degradation of the charge specific capacity of the LCO‖LE gel‖Li coin cell is observed, with a retention of only 85.9%; while the LCO‖c-PEGR gel‖Li coin cell exhibits a high capacity retention of 96.2%. Therefore, compared the LCO‖c-PEGR gel‖Li coin cell, the LCO‖c-PEGR gel‖Li coin cell provided by the present invention has excellent flexibility.

The hydroxyl groups of the glyceryl ether epoxy resin are confined to the main chain of the cross-linked polymer, and thus the freedom of movement of the hydroxyl groups is restricted, which greatly reduced the possibility of oxidation of the hydroxyl groups of the glyceryl ether epoxy resin. Therefore, the oxidation stability of the glyceryl ether epoxy resin is significantly improved. In one embodiment, experiments show that the oxidation potential of the c-PEGR can reach 4.36V, much greater than the oxidation potential of the existing glyceryl ether epoxy resin electrolyte containing ether oxygen groups.

In one embodiment, a quasi-static voltammetry is used to test the oxidation potential of the lithium ion battery electrolyte 100. The method of testing the oxidation potential of the lithium ion battery electrolyte 100 using the quasi-static voltammetry comprises:

step (P1): arranging the lithium ion battery electrolyte 100 between a working electrode and an auxiliary electrode to form an electrolytic cell;

step (P2): applying a first voltage $U_1$ between the working electrode and the auxiliary electrode for a time $\Delta t$;

step (P3): applying a second voltage $U_2$ between the working electrode and the auxiliary electrode for the time $\Delta t$, wherein $U_2=U_1+\Delta U$;

step (P4): applying a third voltage $U_3$ between the working electrode and the auxiliary electrode for the time $\Delta t$, wherein $U_3=U_2+\Delta U$; likewise, applying a nth voltage $U_n$ between the working electrode and the auxiliary electrode for the time $\Delta t$, to obtain a change curve of a current and an electric potential of the electrolytic cell with time, wherein $U_n=U_{(n-11)}+\Delta U$, and n is an integer greater than or equal to 4; and step (P5): obtaining the oxidation potential of the lithium ion battery electrolyte 100 according to the change curve of the current and the electric potential of the electrolytic cell with time.

In the step (P1), the working electrode and the auxiliary electrode can be any working electrode and auxiliary electrode commonly used in lithium ion batteries. In one embodiment, the working electrode is a stainless steel plate, and the auxiliary electrode is a lithium foil.

In the step (P2), the first voltage $U_1$ is ranged from 1.0V to 4.0 V. The first voltage $U_1$ can be selected according to a material of the working electrode and a material of the auxiliary electrode. In one embodiment, the first voltage $U_1$ is 3.0V. The time $\Delta t$ is ranged from 150 seconds to 300 seconds. In one embodiment, the time $\Delta t$ is 150 seconds.

In the step (P3), the smaller a value of $\Delta U$, the smaller a test error. In order to balance the test error and test time, in one embodiment, the $\Delta U$ is ranged from 0.01V to 0.05V. In one embodiment, the $\Delta U$ is 0.02V.

In the step (P4), there is a turning point where a slope changes sharply in the change curve of the current and the electric potential of the electrolytic cell with time.

In the step (P5), the oxidation potential of the lithium ion battery electrolyte 100 is a voltage according to the turning point where a slope changes sharply in the change curve of the current and the electric potential of the electrolytic cell with time. Specifically, a first tangent line is drawn at a start point of the change curve of the current and the electric potential of the electrolytic cell with time, a second tangent line is drawn at an end point of the change curve of the current and the electric potential of the electrolytic cell with time, and a voltage corresponding to an intersection of the first tangent line and second tangent line is the oxidation potential of the lithium ion battery electrolyte 100.

A test time of the quasi-static voltammetry is determined according to the change curve of the current and electric potential of the electrolytic cell over time, when the turning point where the slope changes sharply in the change curve is appeared, the quasi-static voltammetry can be stopped. In one embodiment, after the turning point where the slope changes sharply in the change curve is appeared, the quasi-static voltammetry can also be continue to test for a time. In one embodiment, the test time of the method of testing the oxidation potential of the lithium ion battery electrolyte 100 using the quasi-static voltammetry is 14000 seconds.

Figure 15:
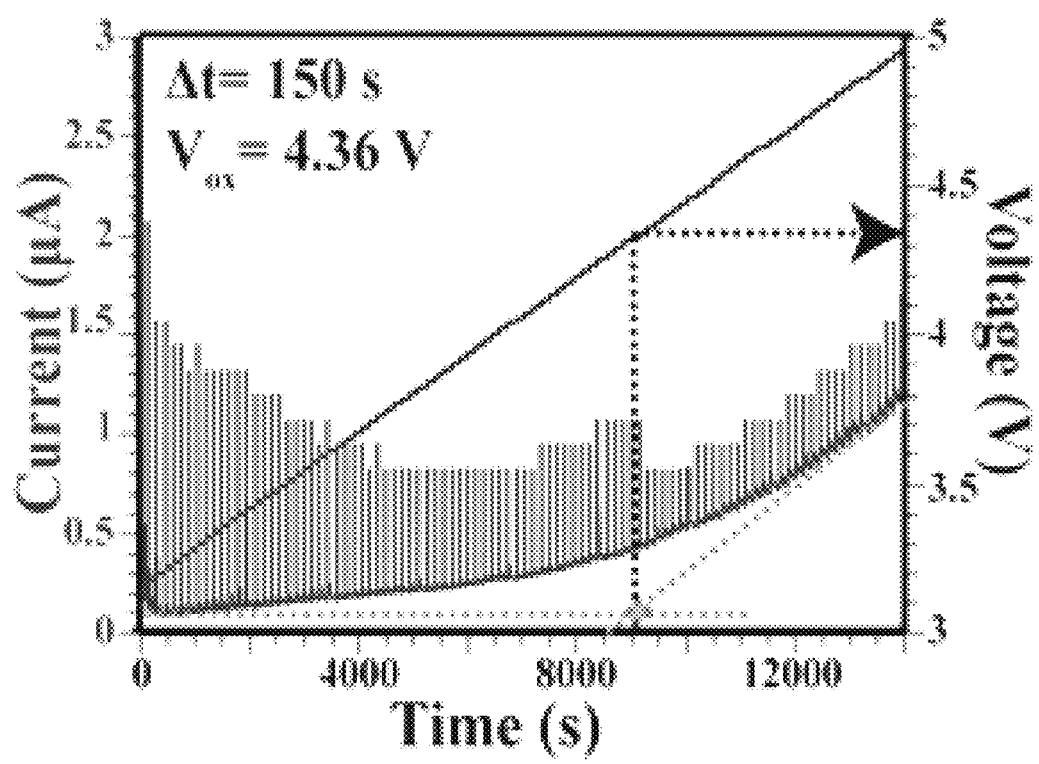
FIG. 15 shows a curve of current and potential of a c-PEGR gel electrolyte of one embodiment changes with time obtained by a quasi-static voltammetry.

FIG. 15 is a curve of current and potential changes with time obtained by using the quasi-static voltammetry to test a c-PEGR gel electrolyte. It can be seen that from FIG. 15, the oxidation potential of the c-PEGR gel electrolyte measured by the quasi-static voltammetry is 4.36V. It can also be seen that from FIG. 15, the test time of the method of testing the oxidation potential of the lithium ion battery electrolyte 100 using the quasi-static voltammetry is 14000 seconds.

During testing the oxidation potential of the lithium ion battery electrolyte 100, due to staying at each voltage for the time $\Delta t$, and the time $\Delta t$ guarantees that the kinetics of electron transport is fully carried out, the electrons involved in the oxidation can completely migrate to the cathode within the time $\Delta t$, an information about each voltage value can be completely fed back without obvious hysteresis. Therefore, the quasi-static voltammetry is more accurate than the oxidation potential of the electrolyte measured by the conventional linear sweep voltammetry (LSV). Especially when testing the oxidation potential of poor conductors, such as polymers, the quasi-static voltammetry of the present invention has more advantages.

Figure 16:
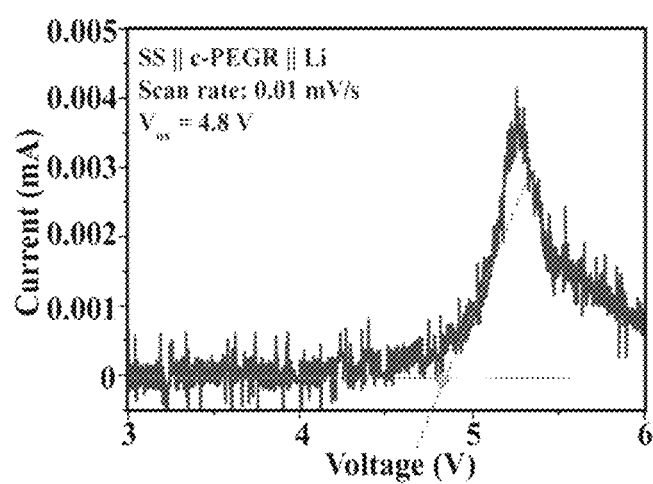
FIG. 16 shows an oxidation potential of the c-PEGR gel electrolyte in FIG. 15 at an extremely slow scan rate of 0.01 mVs$^{-1}$ using a conventional LSV method.

FIG. 16 demonstrates the oxidation potential of the c-PEGR gel at an extremely slow scan rate of $0.01$ $mVs^{-1}$ using the conventional LSV method, but it still only exhibits the oxidation potential of an internal electrolyte of c-PEGR gel rather than the oxidation potential of the c-PEGR gel. Further, the conventional LSV method takes tens of times longer than the quasi-static voltammetry at a scan rate of $0.01$ $mVs^{-1}$ and still has not shown any significant improvement, that is, the conventional LSV method takes much longer time to measure the oxidation potential of polymers, and an accuracy of the measurement results is lower. Therefore, compared with the conventional LSV method, using the quasi-static voltammetry of the present invention to measure the oxidation potential of the polymer can greatly shorten the test time and improve the accuracy of the measurement result.

The quasi-static voltammetry is not limited to test the oxidation potential of the lithium ion battery electrolyte 100. The quasi-static voltammetry can also be applied to an oxidation potential of other electrolytes, especially an oxidation potential of polymer electrolytes with poor conductivity. When the quasi-static voltammetry is used to test other electrolytes, the lithium ion battery electrolyte 100 in step (P1)-step (P5) is replaced with other electrolytes.

Figure 17:
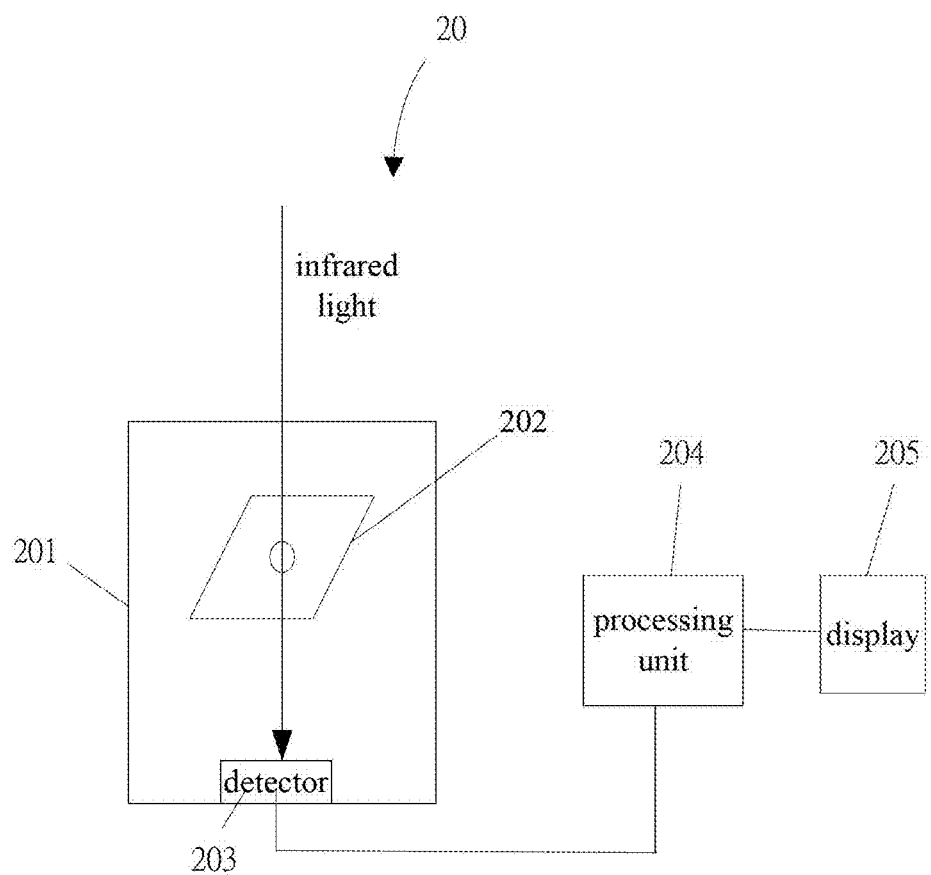
FIG. 17 shows a schematic structural diagram of one embodiment of a test device.

Referring to FIG. 17, a test device 20 for testing the oxidation potential of the lithium ion battery electrolyte 100 is provided. The test device 20 measures the oxidation potential of the lithium ion battery electrolyte 100 through a real-time dynamic infrared spectroscopy of the lithium ion battery electrolyte 100.

The test device 20 comprises a cavity 201, a test unit 202, a detector 203, a processing unit 204, and a display 205. The test unit 202 and the detector 203 are located in the cavity 201. An intensity of the infrared light detected by the detector 203 is transmitted to the processing unit 204, and after the intensity is processed by the processing unit 204, an infrared spectrum of the lithium ion battery electrolyte 100 is obtained on the display 205.

Figure 18:
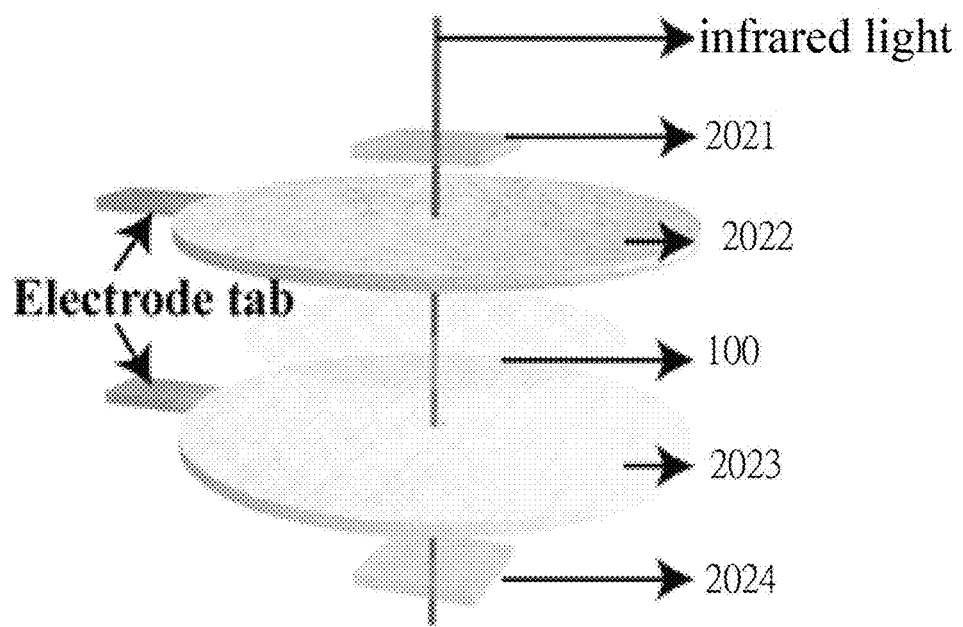
FIG. 18 shows a schematic structural diagram of a test unit of the test device in FIG. 17.

Referring to FIG. 18, the test unit 202 comprises a first infrared window 2021, a positive plate 2022, a negative plate 2023, and a second infrared window 2024. The first infrared window 2021, the positive plate 2022, the negative plate 2023, and the second infrared window 2024 are stacked with each other. The positive plate 2022 comprises a first through hole (not marked). The negative plate 203 comprises a second through hole (not marked). The first through hole and the second through hole penetrate each other, the first infrared window 201 covers the first through hole, and the second infrared window 2024 covers the second through hole. The lithium ion battery electrolyte 100 is located between the positive electrode plate 202 and the negative electrode plate 203, and an infrared light beam passes through the first infrared window 201, the first through hole, the lithium ion battery electrolyte 100, the second through hole, and the second infrared window 2024 in sequence and then is detected by the detector 203.

The detector 203 can be any commonly used infrared light detector. The processing unit 204 can be a computer processing unit for performing mathematical operations on the intensity of the infrared light detected by the detector 203.

A material of the positive electrode plate 2022 is a material that cannot conduct lithium ions. For example, the positive electrode plate 2022 can be a platinum foil, a stainless steel plate, or the like. In one embodiment, the positive plate 2022 is the stainless steel plate.

A material of the negative plate 2023 is a lithium foil.

The positive plate 2022 and the negative plate 2023 are electrically connected to an external circuit. The external circuit applies a voltage to the lithium ion battery electrolyte 100. The voltage of the lithium ion battery electrolyte 100 is changed by changing a voltage between the positive electrode plate and the negative electrode plate applied by the external circuit. The positive plate 2022 can further comprise a positive tab (not shown) extending out of the positive plate 2022, and the negative plate 2023 can further comprise a negative tab (not shown) extending out of the negative plate 2023. The positive electrode tab and the negative electrode tab are used to electrically connect with the external circuit.

The materials of both the first infrared window 2021 and the second infrared window 2024 can be commonly used infrared windows. In one embodiment, the first infrared window 2021 and the second infrared window 2024 are both potassium bromide (KBr) windows. In other embodiments, the first infrared window 2021 is installed in the first through hole 2021, and the second infrared window 2024 is installed in the second through hole 2031.

In one embodiment, the test unit 202 utilizes a pouch cell, two through holes are punched in an aluminum plastic film of the pouch cell, the two KBr windows are adhered to the aluminum plastic film by an epoxy glue, and the two KBr windows cover the two through holes respectively, to ensure airtightness and that the infrared beam can be transmitted.

Since the first through hole and the second through hole have no voltage, under a condition that the infrared beam can be penetrated, the first through hole and the second through hole cannot be too large. In one embodiment, a diameter of the first through hole and the second through hole is ranged from 0.05 mm to 0.2 mm. In one embodiment, the diameter of both the first through hole and the second through hole are 0.1 mm.

A method of testing the oxidation potential of the lithium ion battery electrolyte 100 using the testing device 20 is also provided. The method comprises:
step (R1): providing the test device 20;
step (R2): changing the voltage between the positive plate 202 and the negative plate 203 through the external circuit, and observing the infrared spectra of the lithium ion battery electrolyte 100 in real time under different voltages through the display 205; and
step (R3): obtaining the oxidation potential of the lithium ion battery electrolyte 100, wherein the oxidation potential of the lithium ion battery electrolyte 100 is a corresponding potential when a hydroxyl characteristic peak in the infrared spectrum disappears.

Figure 19:
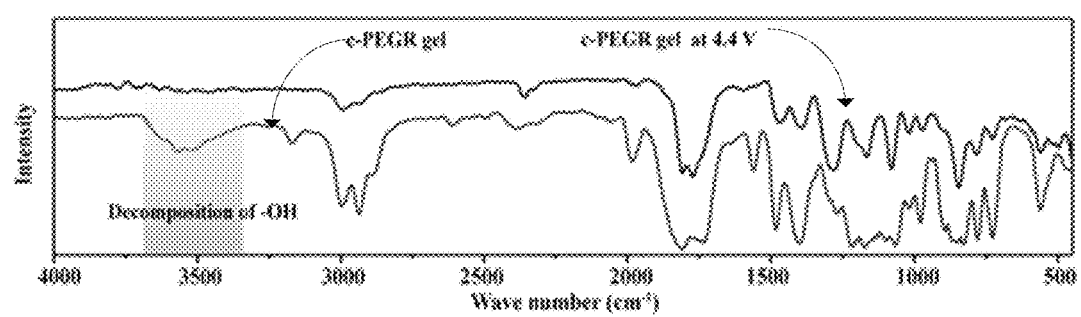
FIG. 19 shows an infrared spectrum of a c-PEGR gel of one embodiment during testing an oxidation potential of the c-PEGR gel by the testing device.

FIG. 19 shows an infrared spectrum of the c-PEGR gel during testing the oxidation potential of the c-PEGR gel by the testing device 20. It can be seen that from FIG. 19, when the voltage is 4.4V, a peak at 3500 $cm^{-1}$ in the infrared spectrum disappear significantly, the peak at 3500 $cm^{-1}$ corresponds to a decomposition of hydroxyl in the c-PEGR gel. It illustrates that the c-PEGR gel electrolyte is oxidized when the voltage is 4.4V, which fits well with the result of 4.36 V by the quasi-static voltammetry, and further verifies the accuracy of the quasi-static voltammetry to test the oxidation potential of polymer electrolytes.

The testing device 20 can also be used to test an oxidation potential of other electrolytes, especially an oxidation potential of polymer electrolytes with poor conductivity. When the testing device 20 is used to test the oxidation potential of other electrolytes, the lithium ion battery electrolyte 100 in step (R1)-step (R5) is replaced with other electrolytes. In one embodiment, the easily oxidizable group in other electrolytes is a group other than the hydroxyl group, when the characteristic peak of the easily oxidizable group in the infrared spectrum disappears, the corresponding potential is the oxidation potential of the other electrolytes.

The testing device and the method for testing the oxidation potential of the electrolyte using the testing device can test the oxidation potential of the electrolyte in situ, dynamically and in real time, especially test the oxidation potential of polymer electrolytes with poor conductivity, which can not achieve by the existing methods.

The lithium ion battery electrolyte is a glyceryl ether epoxy resin gel, the glyceryl ether epoxy resin gel is polymerized by a polyglyceryl ether-based reactant modified with terminal group (epoxy group) and a polyglyceryl ether-based reactant modified with terminal group (amino group), and the glyceryl ether epoxy resin contains the ether oxygen groups. Therefore, the glyceryl ether epoxy resin has excellent flexibility. The glyceryl ether epoxy resin has a cross-linked three-dimensional network structure, and thus the glyceryl ether epoxy resin has excellent mechanical properties and a strong structure. And thus, the lithium ion battery electrolyte also has excellent mechanical properties and strong structure. The glyceryl ether epoxy resin has a cross-linked three-dimensional network structure, and thus the glyceryl ether epoxy resin has excellent mechanical properties and a strong structure. The hydroxyl groups of the glyceryl ether epoxy resin are confined to the main chain of the glyceryl ether epoxy resin; and thus a freedom of movement of the hydroxyl groups is restricted, which greatly reduced the possibility of oxidation of the hydroxyl groups of the glyceryl ether epoxy resin. Therefore, the oxidation stability of the glyceryl ether epoxy resin is significantly improved, and the oxidation potential of the lithium ion battery electrolyte can reach 4.36V. Furthermore, an ethylene oxide (EO) and a propylene oxide (PO) structure are remained on the main chain of the glyceryl ether epoxy resin; therefore, the lithium ion battery electrolyte has excellent compatibility with the Li metal anode.

It is to be understood that the above-described embodiments are intended to illustrate rather than limit the present disclosure. Variations may be made to the embodiments without departing from the spirit of the present disclosure as claimed. Elements associated with any of the above embodiments are envisioned to be associated with any other embodiments. The above-described embodiments illustrate the scope of the present disclosure but do not restrict the scope of the present disclosure.

Depending on the embodiment, certain of the steps of a method described may be removed, others may be added, and the sequence of steps may be altered. The description and the claims drawn to a method may include some indication in reference to certain steps. However, the indication used is only to be viewed for identification purposes and not as a suggestion as to an order for the steps.

What is claimed is:

1. A test device for testing an oxidation potential of an electrolyte comprising:
   a cavity;
   a detector located in the cavity;
   a test unit located in the cavity comprising:
      a positive plate comprising a first through hole;
      a negative plate comprising a second through hole, wherein the first through hole and the second through hole penetrate each other;
      a first infrared window covering the first through hole;
      a second infrared window covering the second through hole, wherein the first infrared window, the positive plate, the negative plate, and the second infrared window are stacked with each other; and
      an electrolyte located between the positive electrode plate and the negative electrode plate, wherein an infrared light beam passes through the first infrared window, the first through hole, the electrolyte, the second through hole, the second infrared window in sequence and then is detected by the detector;
   a processing unit; and
   a display,
   wherein an intensity of an infrared light detected by the detector is transmitted to the processing unit and then processed by the processing unit, an infrared spectrum of the electrolyte is displayed on the display.

2. The test device of claim 1, wherein the positive plate is a stainless steel plate and the negative plate is a lithium foil.

3. The test device of claim 1, wherein the first infrared window and the second infrared window are both potassium bromide (KBr) windows.

4. The test device of claim 3, wherein the test unit utilizes a pouch cell comprising an aluminum plastic film, the first through hole and the second through hole are punched in the aluminum plastic film, each of the KBr windows is adhered to the aluminum plastic film by an epoxy glue and functions as the first infrared window and the second infrared window respectively.

5. The test device of claim 1, wherein a diameter of each of the first through hole and the second through hole ranges from 0.05 mm to 0.2 mm.

6. The test device of claim 1, wherein the positive plate further comprises a positive tab extending out of the positive plate, and the negative plate further comprises a negative tab extending out of the negative plate.

7. The test device of claim 1, wherein the electrolyte is a polymer electrolyte.

8. The test device of claim 7, wherein the electrolyte is a glyceryl ether epoxy resin gel electrolyte, and the glyceryl ether epoxy resin gel electrolyte comprises:
   a glyceryl ether epoxy resin comprising ether oxygen groups, wherein the glyceryl ether epoxy resin is a cross-linked polymer obtained by a ring-opening reaction of a glyceryl ether polymer and a polyamine compound, the glyceryl ether polymer is a glycidyl ether polymer comprising at least two epoxy groups, and the polyamine compound comprises at least two amine groups; the cross-linked polymer is a cross-linked three-dimensional network structure, the cross-linked polymer comprises a main chain and a plurality of hydroxyl groups, and the plurality of hydroxyl groups are located on the main chain; and an epoxy structure of the glyceryl ether polymer is located on the main chain; and
   and an electrolyte comprising a lithium salt and a non-aqueous solvent, wherein the lithium salt is interspersed in the cross-linked three-dimensional network structure of the glyceryl ether epoxy resin, and the lithium salt and the glyceryl ether epoxy resin are dispersed in the non-aqueous solvent.

9. The test device of claim 8, wherein the plurality of hydroxyl groups is restricted to the main chain of the cross-linked polymer and unable to move freely.

10. The test device of claim 8, wherein the glyceryl ether polymer is poly (ethylene glycol) diglycidyl ether, and a structural formula of the poly (ethylene glycol) diglycidyl ether is $C_3H_5O_2$—$(C_2H_4O)_n$—$C_3H_5O$, wherein n is an integer greater than or equal to 1.

11. The test device of claim 10, wherein a molecular weight of the poly (ethylene glycol) diglycidyl ether ranges from 200 to 600.

12. The test device of claim 8, wherein the polyamine compound is polyether amine, and a structural formula of the polyether amine is $CH_3CH(NH_2)CH_2[OCH_2CH(CH_3)]_nNH_2$, wherein n is an integer greater than or equal to 1.

13. The test device of claim 12, wherein a molecular weight of the polyether amine ranges from 1500 to 3000.

14. The test device of claim 8, wherein the glyceryl ether polymer is the poly (ethylene glycol) diglycidyl ether, and the polyamine compound is polyether amine, a chemical reaction formula of the ring-opening reaction of the poly (ethylene glycol) diglycidyl ether and the polyamine compound is:

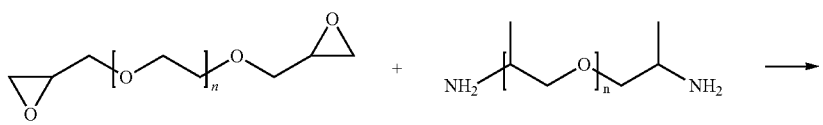

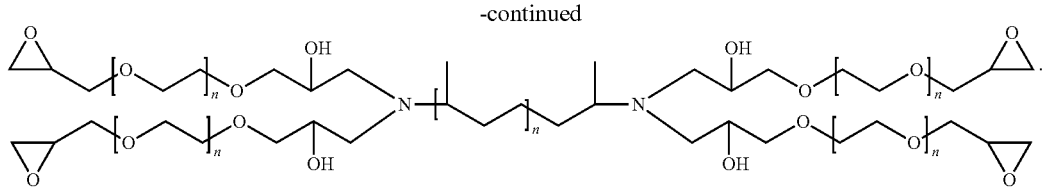

15. A method of testing an oxidation potential of an electrolyte comprising:
    step (S1): providing a test device comprising:
        a cavity;
        a detector located in the cavity; a test unit located in the cavity comprising:
            a positive plate comprising a first through hole;
            a negative plate comprising a second through hole, wherein the first through hole and the second through hole and then each other;
            a first infrared window covering the first through hole;
            a second infrared window covering the second through hole, wherein the first infrared window, the positive plate, the negative plate, and the second infrared window are stacked with each other; and
            an electrolyte located between the positive electrode plate and the negative electrode plate, wherein an infrared light beam passes through the first infrared window, the first through hole, the electrolyte, the second through hole, and the second infrared window in sequence and then is detected by the detector;
        a processing unit; and
        a display,
        wherein an intensity of an infrared light detected by the detector is transmitted to the processing unit and then processed by the processing unit, an infrared spectrum of the electrolyte is di splayed on the display;
    step (S2): changing a voltage between the positive plate and the negative plate through an external circuit, and observing the infrared spectrum of the electrolyte in real time under different voltages through the display; and
    step (S3): obtaining the oxidation potential of the electrolyte, wherein the oxidation potential of the electrolyte is a corresponding potential when a characteristic peak of an reference oxidized group in the infrared spectrum disappears.

16. The method of claim 15, wherein the electrolyte is a glyceryl ether epoxy resin gel electrolyte, and the glyceryl ether epoxy resin gel electrolyte comprises:
    a glyceryl ether epoxy resin comprising ether oxygen groups, wherein the glyceryl ether epoxy resin is a cross-linked polymer obtained by a ring-opening reaction of a glyceryl ether polymer and a polyamine compound, the glyceryl ether polymer is a glycidyl ether polymer comprising at least two epoxy groups, and the polyamine compound comprises at least two amine groups; the cross-linked polymer is a cross-linked three-dimensional network structure, the cross-linked polymer comprises a main chain and a plurality of hydroxyl groups, and the plurality of hydroxyl groups are located on the main chain; and an epoxy structure of the glyceryl ether polymer is located on the main chain; and
    an electrolyte comprising a lithium salt and a non-aqueous solvent, wherein the lithium salt is interspersed in the cross-linked three-dimensional network structure of the glyceryl ether epoxy resin, and the lithium salt and the glyceryl ether epoxy resin are dispersed in the non-aqueous solvent.

17. The method of claim 16, wherein the plurality of hydroxyl groups is restricted to the main chain of the cross-linked polymer and unable to move freely.

18. The method of claim 16, wherein the reference oxidized group is a hydroxyl group.

* * * * *